United States Patent [19]

Foley et al.

[11] Patent Number: 5,012,803
[45] Date of Patent: May 7, 1991

[54] MODULAR MEDICATION INHALER

[75] Inventors: Martin P. Foley, London, Canada; Exequiel D. Cruz, Arlington Heights, Ill.

[73] Assignee: Trudell Medical, London, Canada

[21] Appl. No.: 319,282

[22] Filed: Mar. 6, 1989

[51] Int. Cl.⁵ ............................................ A61M 11/00
[52] U.S. Cl. ............................ 128/200.23; 128/200.14; 128/203.29
[58] Field of Search ................ 128/200.14–200.18, 128/200.23–200.24, 203.12, 203.13, 203.15, 203.29–207.14, 911, 912, 204.18, 206.22, 206.23, 206.24, 207.15, DIG. 26, 202.28, 202.29, 203.11, 202.27

[56] References Cited

U.S. PATENT DOCUMENTS

| | | | |
|---|---|---|---|
| 1,378,481 | 5/1921 | Mobley | 128/200.23 |
| 2,302,707 | 11/1942 | Mejean | 128/202.27 |
| 3,184,115 | 5/1965 | Meshberg | 128/200.23 |
| 3,320,952 | 5/1967 | Wright | 128/200.23 |
| 3,490,452 | 1/1970 | Greenfield | 128/200.23 |
| 4,146,034 | 3/1979 | Gupta | 128/207.14 |
| 4,470,412 | 9/1984 | Nowacki et al. | 128/200.18 |
| 4,484,577 | 11/1984 | Sackner et al. | 128/203.29 |
| 4,506,665 | 3/1985 | Andrews et al. | 128/203.29 |
| 4,625,721 | 12/1986 | Levine et al. | 128/202.27 |
| 4,832,015 | 5/1989 | Nowacki et al. | 128/205.23 |
| 4,852,561 | 8/1989 | Sperry | 128/200.23 |

FOREIGN PATENT DOCUMENTS

| | | | |
|---|---|---|---|
| 540488 | 10/1941 | United Kingdom | 128/200.14 |
| 622391 | 5/1949 | United Kingdom | 128/200.14 |

Primary Examiner—Edgar S. Burr
Assistant Examiner—Kimberly L. Asher
Attorney, Agent, or Firm—Robert M. Wolters

[57] ABSTRACT

A medication inhaler is provided having a cylindrical body usable with different inlet and outlet fittings at the opposite ends thereof. An inlet end fitting is provided with inner and outer cylindrical flanges gripping the upstream end of the cylindrical body and adapted to receive structure for misting medication into said cylindrical body. The downstream or outlet end fitting snaps over the downstream end of the cylindrical body and is provided with an axially extending protrusion impinging against and securing a flexible diaphragm to an inwardly directed flange at the exit end of the cylindrical body. The outlet end fitting may take different forms such as a mouthpiece to fit into a patient's mouth, a mask to fit over a patient's mouth and nose, or a connection for flexible tubing leading to an endotracheal tube.

11 Claims, 3 Drawing Sheets

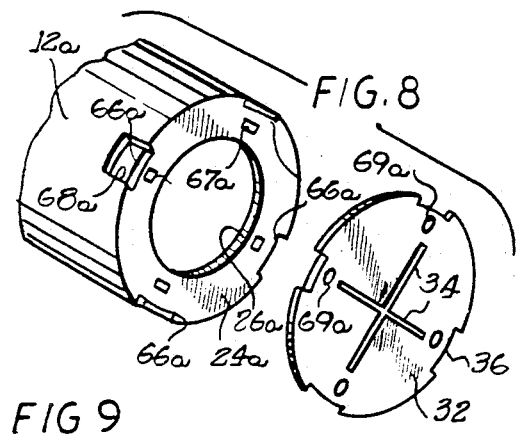
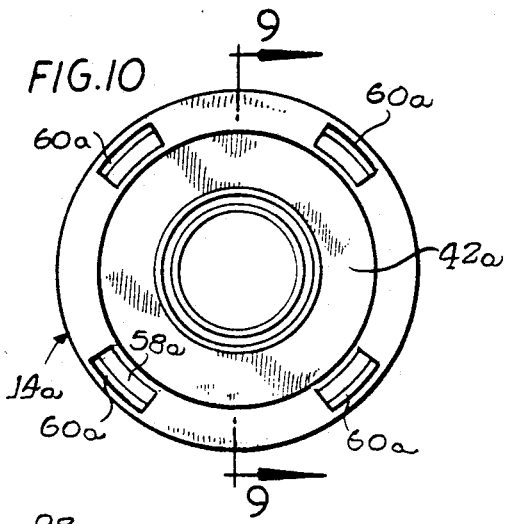
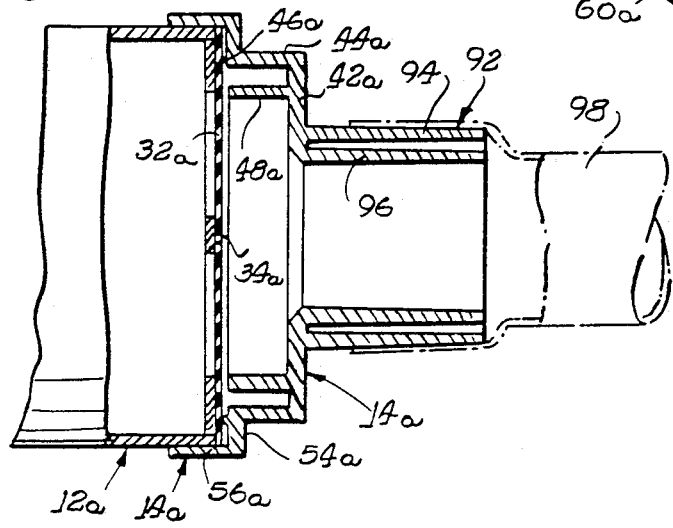
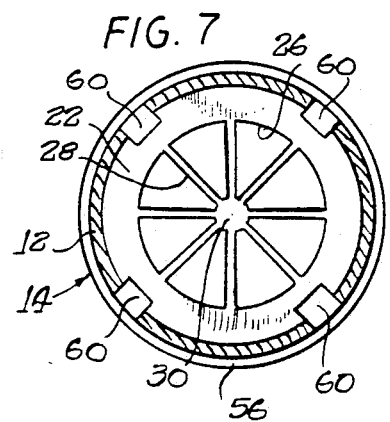
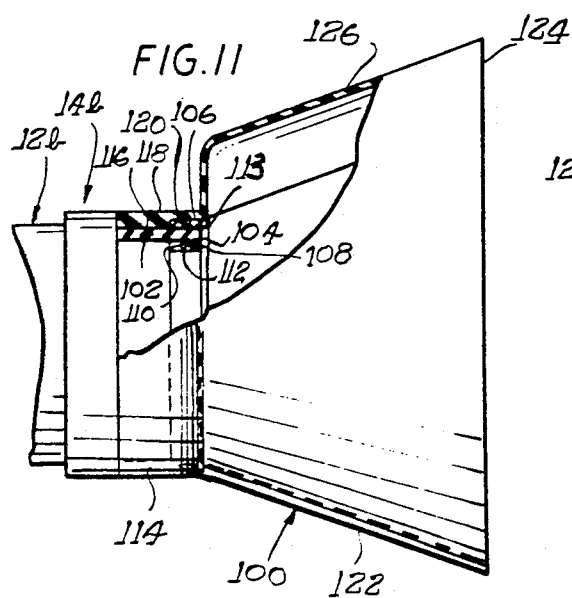
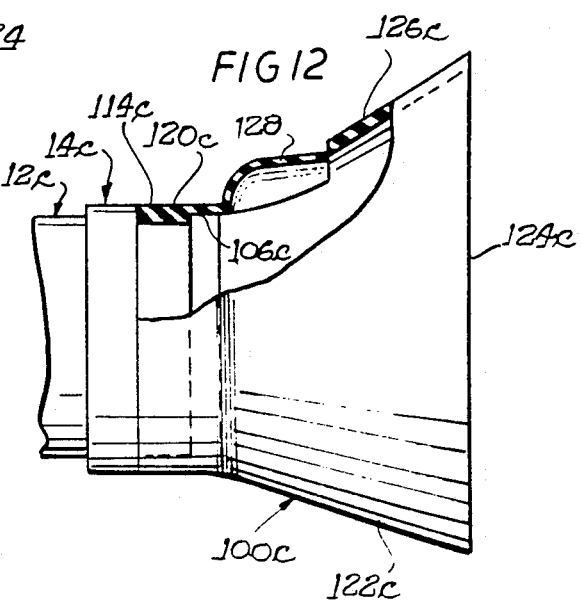

MODULAR MEDICATION INHALER

DESCRIPTION OF THE INVENTION

Metered dose inhalers are well known in which a small canister is packed with epinephrine or other suitable bronchodilator. The canister is held in a generally L-shaped fitting, and an axial push on the canister causes a metered dose of medication to be ejected into the fitting in spray from. Ideally the spray should be in the form of a fine mist so as to pass completely into the bronchial tubes for dilation thereof. Such medication is commonly used for asthmatic relief, or for other times when brochial dilation is required. The person to whom the medication is administered inhales from the fitting through his mouth.

It often happens that the medication is not thoroughly misted, and there are large drops which simply pass into the stomach, and have no effect on bronchial dilation. It is known that a cylindrical inhaler device can be used in combination with the L-shaped fitting for improved results. The L-shaped fitting is inserted into an elastomeric diaphragm at the upstream or entering end of the cylinder, and a mouthpiece is provided at the exit or downstream end. A one-way diaphragm is provided adjacent to the mouthpiece so that the medication can be inhaled through the mouth, but exhalation will not cause air to be passed back through the cylinder. A satisfactory apparatus of this type is shown in U.S. Pat. No. 4,470,412. It has been found that this apparatus is highly efficient in converting the medication into a mist which is highly effective in reaching the bronchial area.

In the aforesaid patent an elastomeric fitting is provided at the upstream end of the cylinder to receive the L-shaped fitting carrying the medication canister. At the downstream end a mouthpiece to be received in the mouth is provided. Such a device has also been found effective with a pediatric mask at the downstream end, see application Ser. Nos. 058,683 filed June 4, 1987 and 07/164,230 filed May 19, 1988. It has more recently been determined that the same structure can be used with an adult or a pediatric mask, as disclosed hereinafter in this application, and that much of the same basic apparatus can be used as an inline inhaler connected between an air/oxygen supply and an endotracheal tube inserted into a patient's trachea, as also disclosed in this application.

OBJECTS AND SUMMARY OF THE PRESENT INVENTION

It is the object of the present invention to provide a modular medication inhaler in which basic structure is selectively assembled with respective fittings for different types of medication administration.

More particularly, it is an object of the present invention to provide a modular medication inhaler in which a basic cylindrical chamber and diaphragm can be provided with different inlet and outlet fittings for different administration of medication, all of which interfit with the basic cylindrical chamber in the same manner.

In effecting the foregoing and other objects in accordance with this invention a cyclindrical chamber is provided with an open upstream end, and with a lower end having an inwardly directed, ring-like flange which is either open in the center or provided with a spider. The upstream end alternatively may be provided with an elastometric fitting for receiving an L-shaped fitting with a metered dose inhaler, or it may be provided with a specific substantially rigid fitting carrying a metered dose inhaler canister and adapted for connection to an air/oxygen supply tube. The downstream or exit end has a diaphragm with a cross-shaped slit therein with the diaphragm clamped against the inwardly directed ring by a part of the outlet fitting. The outlet fitting may comprise a mouthpiece for receipt in the patient's mouth, or it may comprise either a pediatric mask or an adult mask, a part of which clamps the perimeter of the diaphragm against the aforesaid flange. A spider lies immediately adjacent the diaphragm on the upstream side thereof and backs up the slits so that air and medication can be inhaled past the diaphragm, but exhalation will simply force the diaphragm against the spider and cause exhaled air to be exited downstream of the diaphragm. In a further form of the invention the spider is omitted, but the periphery of the diaphragm is still clamped against the inwardly directed flange by a portion of an exit fitting having a tubular exit for connection to an endotracheal tube.

THE DRAWINGS

The present invention will best be understood from the following specification when taken in connection with the accompanying drawings wherein:

FIG. 7 is a cross sectional view taken substantially along the line 7—7 in FIG. 3;

FIG. 8 is a perspective view of the cylindrical body of the present inhalation device and the accompanying diaphragm with the mouthpiece removed;

FIG. 9 is a fragmentary longitudinal sectional view generally similar to FIG. 3 on an enlarged scale and showing a modification of the invention as taken substantially along the line 9—9 in FIG. 10;

FIG. 10 is a right end view of the embodiment of FIG. 9;

FIG. 11 is a fragmentary partial sectional view showing a modification of the invention using an adult inhalation mask;

FIG. 12 is a view similar to FIG. 11 and showing use with a pediatric mask;

DETAILED DISCLOSURE OF THE ILLUSTRATED EMBODIMENTS

Figure 1:
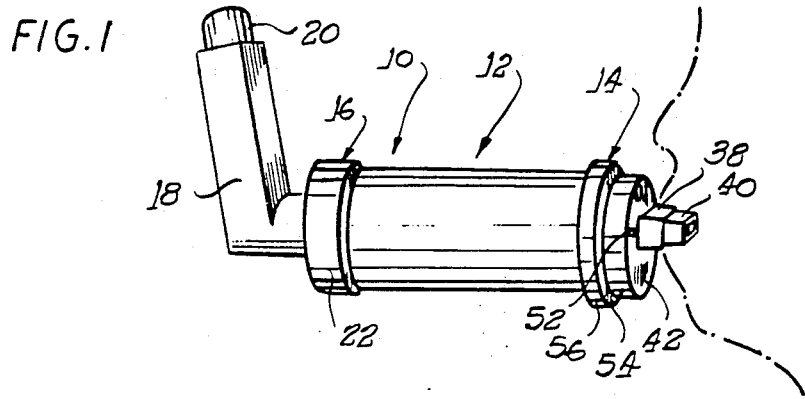
FIG. 1 is a perspective view of one embodiment of the invention.
Figure 2:
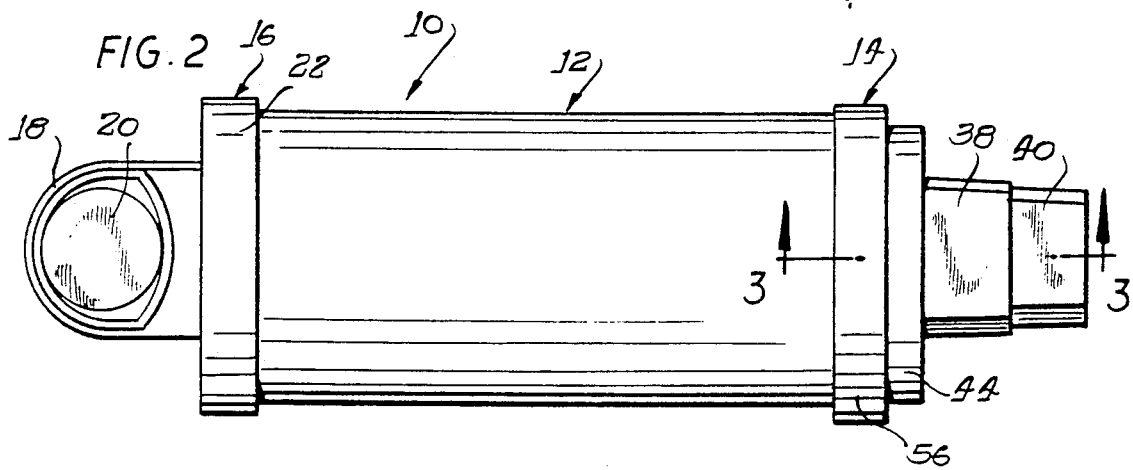
FIG. 2 is a top view on an enlarged scale of the inhalation device shown in FIG. 1.
Figure 6:
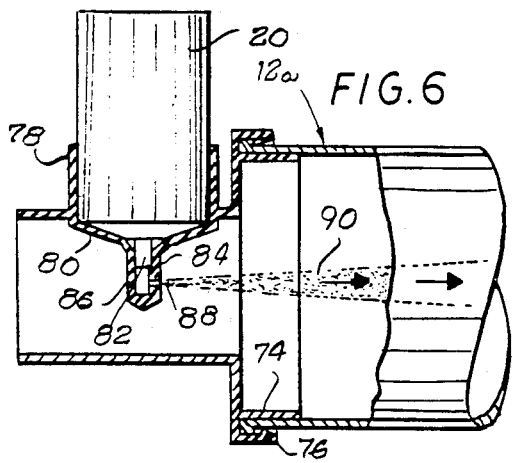
FIG. 6 is a fragmentary sectional view of the left end of a modified form of the present inhalation device.
Figure 3:
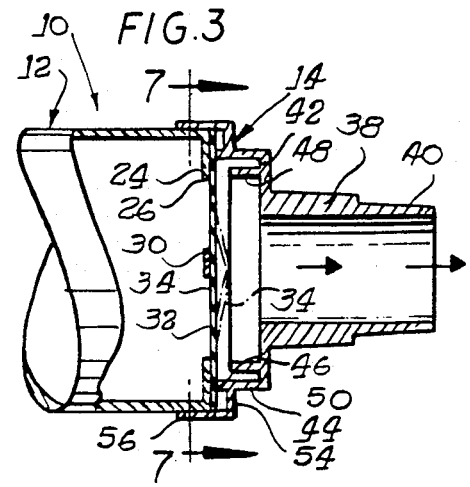
FIG. 3 is a fragmentary longitudinal sectional view taken substantially along the line 3—3 in FIG. 2.
Figure 4:
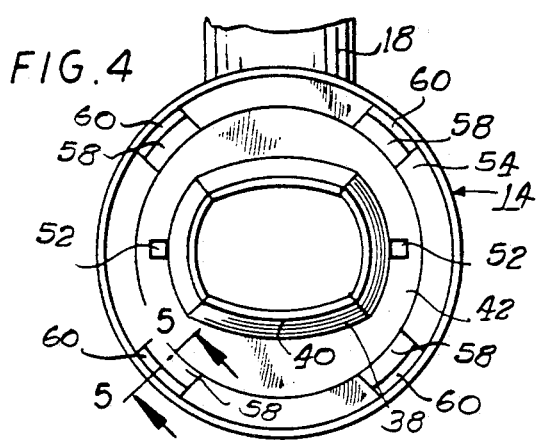
FIG. 4 is an end view of the inhalation device as taken from the right end of FIG. 3.

A modular medication inhaler constructed in accordance with the present invention is shown first in FIGS. 1–3 at 10 and includes an elongated cylindrical, hollow body 12. At the downstream or exit end of the body there is provided an exit fitting 14 designed in part for reception in the human mouth. At the upstream or entering end there is an elastomeric fitting 16 receiving the well known L-shaped adapter or fitting 18, which in turn receives the metered dose canister 20. The inlet or upstream end adapter 16 is shown in detail in copending U.S. Pat. application Ser. No. 07/164,230 filed May 19, 1988, the disclosure of which is herein adapted by reference. In general, the fitting 16 includes a cylindrical outer portion 22 encircling the inlet end of the cylindrical body 12 and having a transverse diaphragm portion with an opening therein receiving the horizontal portion of the L-shaped adapter or elbow 18.

Figure 5:
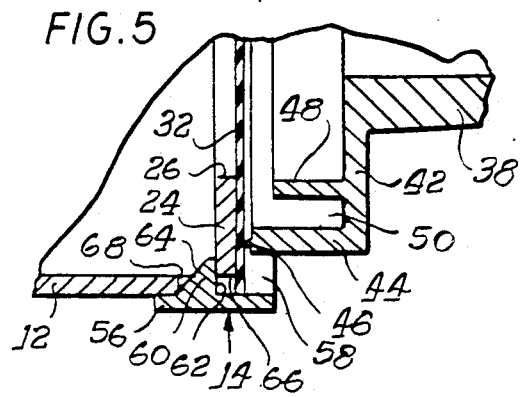
FIG. 5 is an enlarged fragmentary view taken substantially along the line 5—5 in FIG. 4.

At the downstream or exit end of the cylindrical body 12, there is an inwardly directed flange 24 defining a central aperture 26 of substantial diameter relative to the diameter of the cylindrical body 12, see additionally FIGS. 3, 5, and 7. A spider 28 comprising eight radially extending legs is joined at its outer portions to the flange 22 with which it is integrally formed. The inner ends of the spider legs meet at a common center portion 30.

A thin diaphragm 32 (see also FIG. 8) of plastic or elastomeric material lies against the circular flange 24 and is held against this flange by the downstream end fitting 14 as will be brought out more fully hereinafter. The diaphragm is provided with a pair of slits 34 in the form of a cross, and the slits lie against legs of the spider 28. Accordingly, upon inhalation through the end fitting 14 the diaphragm will deflect to the right as shown in FIG. 3 with the slits opening further to permit free air flow. Upon exhalation the diaphragm is forced against the spider and air is not permitted to enter the cylindrical body 12 from the downstream end.

The exit end or downstream end fitting 14 includes a mouthpiece 38 designed for receipt in the human mouth. A reduced end portion 40 of the mouthpiece is provided for receipt of a cap for covering the mouthpiece when not in use. The mouthpiece is relatively wide and not very high. The outer surfaces thereof, and also the corresponding inner surfaces are on circular arcs for best conformity with the human mouth. At the inner or upstream end of the mouthpiece there is an outwardly directed annular flange 42 which carries at its periphery an upstream directed cylindrical portion 44 bearing against the diaphragm 32 to clamp the diaphragm against the flange 24. The flange 42 also supports an inner cylindrical portion 48 of lesser diameter and lesser length than the cylindrical portion 44, but coaxial therewith. This provides a space 50 between cylindrical portions 44 and 48 through which exhaled air can pass to a pair of apertures 52 (FIG. 1) in the flange 42 permitting exhausting of the exhaled air.

On the outside of the outer cylindrical portion 44 and relatively toward the free edge 46 thereof there is provided an annular flange 54 carrying at its outer margin a forwardly (upstream direction) extending cylindrical flange 56 of proper diameter to embrace the end of the cylindrical body 12.

At four equally arcuately spaced locations the flange 54 is provided with arcuately elongated apertures 58 extending radially from the cylindrical portion 44 to the cylindrical portion 56. Teeth 60 are disposed inwardly (upstream) of the apertures 58 on the inner surface of a cylindrical portion 56. The teeth have right angle locking faces 62 and diagonal camming faces 64. Corresponding notches 66a are provided in the flanges 24 of the cylindrical body 12, accompanied by apertures 68a and the cylindrical body, see FIG. 8. The flange 24a preferably has four protrusions received in respective apertures 69a in the diaphragm for improved locating of the diaphragm.

In assembling the foregoing parts all that is necessary is to place the cylindrical body 12 in an upright position, place the diaphragm 32 thereon, and snap the end fitting 14 into place. The teeth 60 are accommodated by the notches 36 in the diaphragm, and snap over the flange 24 into the openings 68a thus locking the exit end fitting 14 in place with the front edge 46 of the cylindrical portion 44 clamping the diaphragm in place. The end fitting 16 is readily pushed on the opposite end of the cylindrical body 12. The apertures 58 in the flange 54 provide accommodation for mold parts necessary to form the teeth 60. However, in the finished product they also have utility in that they provide enhanced flexibility to the cylindrical portion 56 in the vicinity of the teeth 60, thus facilitating snapping the teeth into place in the apertures 68.

A modification of the invention is shown in FIGS. 6 and 8-10. This embodiment of the invention is for use as an inline inhaler in connection with mechanical breathing apparatus. Most parts remain the same or similar, and like parts are identified with numerals similar to those heretofore used with the addition of the suffix a. The upstream or entering end fitting 16a has a tubular inlet 70 adapted to be connected to an oxygen/air hose periodically supplying a mixture of air and oxygen under pressure. This tubular portion joins integrally to a radial flange 72 carrying spaced cylindrical portions 74 and 76 which embrace the entering end of the cylindrical body 12a. The cylindrical body 12a is unchanged from the cylindrical body previously described, except that the spider is omitted therefrom, leaving simply the aperture 26a in the flange 24a. The spider may be eliminated during production of the cylindrical body 12a by an insert in the mold, or it may be molded in place and quickly cut away for the present embodiment.

The tubular inlet 70 is provided with a radially extending well 78 receiving the metered dose canister 20. The inner end of the well is conical at 80 and has a reduced portion for receipt of the nozzle 82 of the canister 20, the nozzle fitting in a recess 84 in a protruding nose 86 at the bottom of the well. The nose is provided with a lateral aperture 88 for exit of a spray or mist 90 of medication from the canister 20. The tubular inlet portion 70 is designed to have a hose or tubing connected thereover which is normally connected to an air/oxygen supply through the usual wye connection providing also for exhalation. Periodically an air/oxygen mixture under pressure is applied and passes through the cylindrical body 12a. It is sometimes necessary to administer a bronchodilator during mechanical ventilation of a patient, and this is done simply by depressing the canister 20 to spray the mist 90 of medication into the cylindrical body 12a just ahead of the entering air/oxygen mixture. It will be understood that the two cylindrical portions 74 and 76 gripping the upstream end of the cylindrical portion provide greater stability in preventing the entering end fitting 16a from popping off from the body when the air/oxygen mixture is supplied under pressure. Preferably, teeth on the outer cylindrical portion engage a rib on the body 12a.

The downstream or exit end fitting 14a is generally similar to that previously disclosed, and like numerals are used to identify similar parts with the addition of the suffix a. The distinction lies in that there is a tubular exit member 92 rather than the mouthpiece, which member is intended to receive a tube of flexible nature leading to an endotracheal tube. The tubular member comprises two concentric and spaced cylinders 94 and 96. This permits association of flexible tubing 98 of different diameters therewith, either exteriorly or interiorly.

Inclusion of the diaphragm 32a with no spider or other backup member is important. Absence of the spider or backup member permits the patient to exhale through the endotracheal tube, and past the inhalation device, and subsequently through a wye connector. However, retention of the diaphragm is important. Medication can be ejected into the inhaler just before a pressure delivery of air/oxygen mixture, and the misted medication will be retained in the cylindrical body or chamber 12a until the pressurized air/oxygen mixture is delivered into the chamber to carry the misted medication past the diaphragm 32a which deflects to the right as heretofore described, thereby to open the slots 34a to pass the medication with the air/oxygen mixture.

The basic structure heretofore described, particularly the cylindrical chamber, the inlet or upstream fitting 16, and the medication dispenser 18, 20 is adapted also for use with an adult inhalation mask 100 as shown in FIG. 11. Many of the parts are the same as or similar to those heretofore described, and such parts are identified by similar numerals with the addition of the suffix b, thereby to avoid repetition of disclosure. An end fitting 14b is similar to the originally disclosed fitting insofar as it snaps onto the end of the cylindrical body or chamber 12b. There is also a part bearing against the diaphragm, such part not being shown. The diaphragm likewise is not shown, as this is not necessary in view of the previous disclosure. The fitting 14b is completed by a cylindrical member 102 in substantially the same position as the previous cylinder 44, the inner end thereof bearing against the diaphragm. The tube or cylinder 102 is somewhat longer than heretofore, and is provided on the interior surface of its outer edge with an inwardly directed circumferential flange 104. A relatively short axial cylinder 106 embraces the outer end of the cylinder 102, which will be noted as tapering inwardly to the right. The cylinder 106 is formed integral with a connecting flange 108 which supports an inner cylinder 110 having a plurality, preferably 4, of inwardly directed teeth 112 which snap behind the flange or ring 104 to hold the cylinder 106, 112 in place on the end of the tapered cylinder 102. The cylindrical structure 106, 108 is provided with apertures 113 similar to the previously disclosed apertures 66, 68 in the cylindrical body 12 provide clearance for molding parts for the teeth 112, and also to provide enhanced flexibility at the respective locations.

The cylindrical body 12 and the exit end fitting 14, as well as exit end fittings 14a and 14b are made of a semi-rigid plastic material. The mask 100 is made of silicone rubber which is relatively flexible and which resists deterioration with age and which further permits sterilization due to its stability at high temperatures. The mask comprises an upstream cylindrical portion 114 having an internal diameter 116 snuggly engaging the tapered cylindrical extension 102, and having a counterbore 118 providing a latching surface or tooth 120 abutting the end of the cylindrical member or collar 106. The mask tapers outwardly from the cylindrical portion 114 at 122 in a form of a conical frustum 122 to a free open edge 124 for impingement against the face of an adult person requiring medication. The mask is axially open as will be apparent. In addition, the mask is provided with a relatively narrow and substantially thinner radial protrusion 126 running from the cylindrical portion 114 to the free outer edge 124. This extension lies over and provides clearance for the nose, thereby permitting sealing of the free edge 124 of the mask to the face of the adult patient. An important feature of the extension or protrusion 126 is that a nurse or other health care person can squeeze the patient's nose through the protrusion 126 to insure that no medication is inhaled into the nose where it is useless, but is inhaled entirely through the mouth where it reaches the bronchial area for patient relief.

Alternatively, the extension or protrusion 126 may be left untouched, and will then serve as a tell-tale, flexing in and out as the patient breathes to indicate that the patient is breathing, should he be unconscious.

A similar pediatric mask is shown in FIG. 12. The pediatric mask is generally similar to that disclosed and claimed in application Ser. No. 07/164230, filed May 19, 1988. The parts are generally similar to those heretofore shown and described herein, and similar numerals are again used, this time with the addition of the suffix c.

Instead of a protrusion or extension along the entire length of the frustoconical portion of the adapter or face mask 100c there is provided a small somewhat shorter extension 126c leading from the free edge 124c and overlying the infant's nose, connecting with a bubble 128 which will flex in and out as the infant breathes, thereby to provide a visual indication that the patient is properly breathing.

Figure 13:
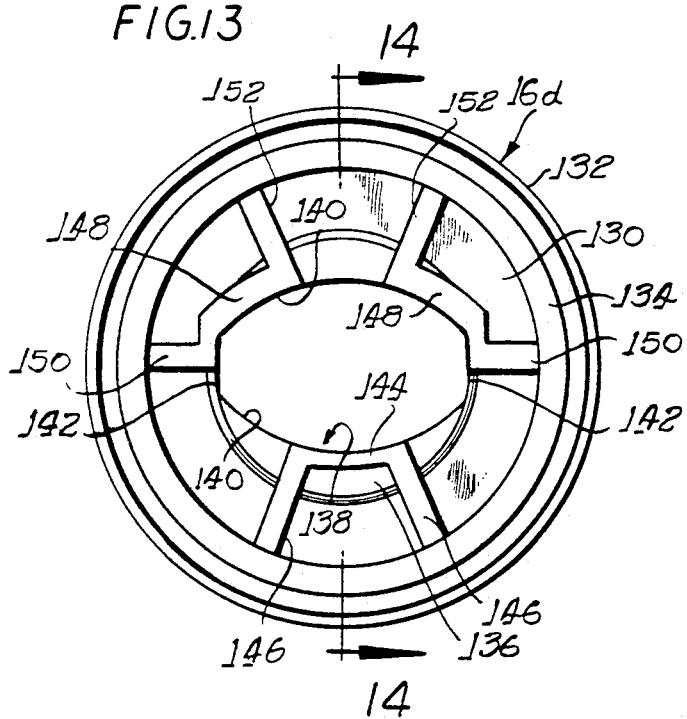
FIG. 13 is a downstream end view of a preferred inlet end fitting.
Figure 14:
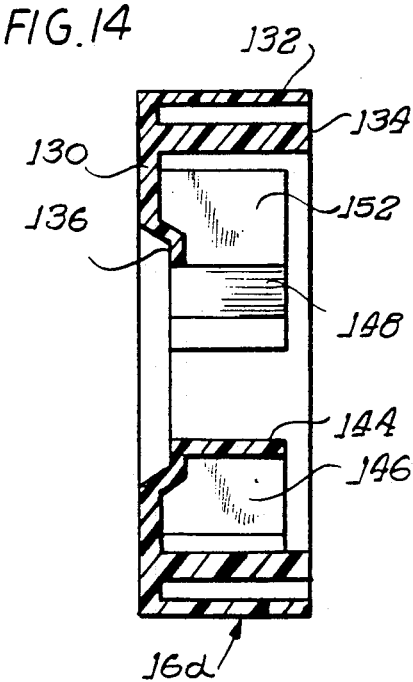
FIG. 14 is an axial sectional view taken substantially along the line 14—14 in FIG. 13.

The upstream or inlet fitting 16 has been referred to heretofore only rather generally. A preferred form of such fitting is shown at 16d in FIGS. 13 and 14. The fitting is circular in shape including a central wall or disk 130, having at the periphery thereof spaced generally cylindrical flanges 132 and 134 intended to lie respectively on the outer surface and inner surface of the cylindrical chamber 12 at the entering end thereof. The center of the disk or wall 130 is inwardly offset at 136 in a circular pattern and is provided with a central aperture 138 having curved upper and lower edges 140 and straight side edges 142. The aperture 138 is sized so as to receive snugly the horizontal end of the L-shaped fitting 18 carrying the medication canister 20.

Inwardly (downstream) of the indented portion 136 of the disk or wall 130 there is an arcuate wall 144 underlying the inner edge 140 of the aperture 138. Axial braces or fins 146 extend from the ends of the arcuate wall 148 out to the inner flange 134. The wall 144 and ribs or braces 146 terminate slightly short of the extremities of the flanges 132 and 134. A pair of additional braces, comprising inner walls 148 having inner surfaces conforming to portions of the upper arcuate edge 140 and portions of the straight side edges 142 are provided at the upper corners of the aperture 138. Horizontal bracing flanges 150 and radially extending bracing flanges 152 extend from the ends of the walls 148 out to the flange 134. These walls and braces extend inwardly the same distance as the wall 144 and braces 146.

The fitting 16d is made of a relatively soft and pliable, yet resilient material which may be a rubber-like or elastomeric material, or resinous plastic; the later, may be referred to as simply plastic.

The specific examples of the present invention as herein shown and described will be understood as forming a part of the present invention insofar as they fall within the spirit and scope of the appended claims.

We claim:

1. A modular medication inhaler comprising a cylindrical body having an axis of rotation and having an upstream entering end and a downstream exit end and open at both ends, an integral inwardly directed peripheral flange at the exit end transverse of said axis of rotation, said flange having an outer surface a fitting on the entering end adapted to receive structure for applying misted medication into said cylindrical body, a flexible diaphragm at said exit end and having a slit therein, said diaphragm flexing and opening said slit upon inhalation for passing air and medication, and a fitting at the exit end of said cylindrical body and secured to said body, said exit end fitting having an outer cylindrical flange snugly encircling said cylindrical body on the exterior of said body, an inwardly directed flange transverse of said axis, and arcuate protruberance means on said inwardly directed fitting flange engaging said diaphragm adjacent the periphery thereof and inwardly of said cylindrical body and clamping said diaphragm against the outer surface of said inwardly directed peripheral flange, and further including retaining means on said cylindrical body, comprising means providing a plurality of apertures arcuately spaced in said cylindrical body and said exit end integral inwardly directed flange and defining retaining edges on said flange, and a plurality of inwardly directed teeth on said exit end fitting cylindrical flange snapped over said retaining means and securing said exit end fitting on said cylindrical body.

2. A modular medication inhaler as set forth in claim 1 wherein said annular protruberance comprises a cylindrical shape.

3. A modular medication inhaler as set forth in claim 1 wherein said exit fitting has an axially extending tubular member on the downstream thereof adapted to receive flexible tubing leading to an endotracheal tube.

4. A modular mediation inhaler as set forth in claim 3 wherein said tubular member comprises a pair of concentric tubes of differing diameter for receiving tubing of different sizes.

5. A modular medication inhaler as set forth in claim 1 wherein said exit end fitting has a wall extending inwardly from said cylindrical flange, said wall having a plurality of apertures therein respectively adjacent the teeth and imparting enhanced flexibility to said teeth.

6. A modular medication inhaler as set forth in claim 1 and further including a spider coplanar with said peripheral flange and extending inwardly therefrom, said spider backing the slit in said diaphragm and preventing exhalation through said cylindrical body.

7. A modular medication inhaler as set forth in claim 6 wherein said exit fitting has an axially extending mouthpiece adapted to be received in the human mouth.

8. A modular medication inhaler as set forth in claim 1 wherein said entering end fitting has an inlet tubular member extending upstream and adapted to receive an air/oxygen supply tube, and lateral inlet means on said tubular member for receiving a measured dose dispenser.

9. A modular medication inhaler as set forth in claim 8 wherein said inlet means comprises a well extending into said tubular member.

10. A modular medication inhaler as set forth in claim 9 wherein said entering end fitting has an opening therein to receive the holder for a measured dose dispenser, and means on said entering end fitting extending axially into said cylindrical body adapted to brace a measured dose inhaler holder, said brace means comprising a plurality of axially extending flanges.

11. A modular medication inhaler as set forth in claim 10 wherein said flanges are interconnected by walls which with said flanges define box-like bracing structure surrounding said opening at least in part.

* * * * *